United States Patent [19]
Orjales-Venero et al.

[11] Patent Number: 5,322,850
[45] Date of Patent: Jun. 21, 1994

[54] ANTIALLERGIC PIPERIDINE DERIVATIVES OF BENZIMIDAZOLE

[75] Inventors: Aurelio Orjales-Venero, Neguri; Victor Rubio-Royo, Guecho, both of Spain

[73] Assignee: Fabrica Espanola de Productos Quimicos y Farmaceuticos, S.A., Leiva-Lamiaco, Spain

[21] Appl. No.: 64,424

[22] Filed: May 21, 1993

[30] Foreign Application Priority Data

Jul. 20, 1992 [ES] Spain ................................. 9201512

[51] Int. Cl.$^5$ ................. A61K 31/445; C07D 401/04
[52] U.S. Cl. ........................................ 514/322; 546/199
[58] Field of Search ......................... 546/199; 514/322

[56] References Cited

U.S. PATENT DOCUMENTS

| 4,988,689 | 1/1991 | Janssens | 546/271 |
| 5,021,433 | 6/1991 | Alminger | 546/271 |
| 5,215,974 | 6/1993 | Alminger | 546/271 |

FOREIGN PATENT DOCUMENTS

| 255161 | 11/1985 | Fed. Rep. of Germany | 546/199 |
| 0001697 | 2/1992 | World Int. Prop. O. | 546/199 |

Primary Examiner—C. Warren Ivy
Assistant Examiner—Celia Chang
Attorney, Agent, or Firm—Birch, Stewart, Kolasch & Birch

[57] ABSTRACT

New piperidine derivatives of benzimidazole of the formula:

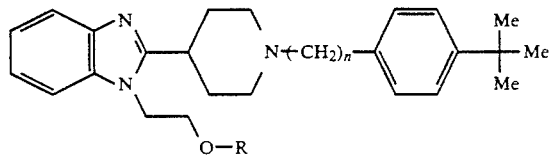

wherein n is 1 or 2 and R is lower alkyl, lower alkenyl or lower cycloalkyl, or a pharmaceutically acceptable salt thereof, are useful antihistaminic and antiallergic agents.

12 Claims, No Drawings

ANTIALLERGIC PIPERIDINE DERIVATIVES OF BENZIMIDAZOLE

DESCRIPTION OF THE INVENTION

The search for effective drugs for the treatment of allergic diseases has experienced a great development in the last few years due to increases in the frequency that these phenomena occur, especially in the developed world, as well as to the lack of truly effective drugs which do not produce side effects.

Allergic diseases are characterized by the release of mediators from the inside of certain cells of the organism; and histamine is one of the most important released mediators. Products antagonizing histamine action have been found to be the most useful for the treatment of illnesses of the allergic type, although most of them have effects on the central nervous system (CNS). Obtaining new antihistamine compounds devoid of effects on the CNS is one of the top priorities of the pharmaceutical industry.

This invention refers to new piperidine derivatives of benzimidazole with high levels of antihistaminic and antiallergic activity and low toxicity. These compounds are represented by formula I, wherein n is 1 or 2 and R is a lower alkyl, lower alkenyl or lower cycloalkyl, such as methyl, ethyl, isopropyl, cyclopropyl and vinyl, as well as the pharmaceutically acceptable acid addition salts thereof.

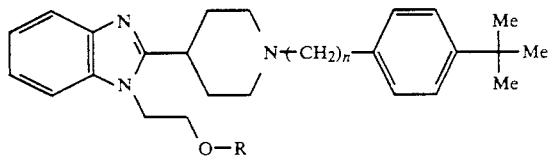

Compounds I may be conveniently prepared by means of a N-alkylation reaction of a N-unsubstituted benzimidazole represented by the general formula II with an

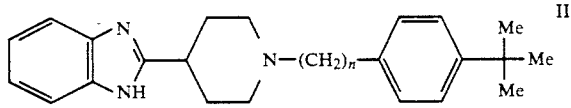

alkylating agent of the type $Y-CH_2-CH_2-O-R'$, where Y is a good leaving group, in the presence of an inorganic base such as a carbonate, a bicarbonate or a hydride of an alkaline metal. The new piperidinbenzimidazoles thus obtained may be transformed into the corresponding salts by treating them in ethanolic solutions with pharmaceutically acceptable acids, such as hydrochloric, hydrobromic, phosphoric, oxalic, propanoic, butanedioic and similar acids.

The following examples illustrate, without limitation, the specific methods employed in production of a representative number of compounds embraced by this invention.

EXAMPLE 1

Preparation of 2-[1-((4-(1,1-dimethylethyl)phenyl)methyl)pipiridin-4-yl]-1-(2-methoxyethyl)-1H-benzimidazole 1.73 g of 2-[1-((4-(1,1-dimethylethyl)phenyl)methyl)-piperidine-4-yl]-1H-benzimidazole are disolved in 15 mililiters of dimethylformamide under a nitrogen atmosphere and 0.24 g of 40% sodium hydride oil solution are added; the resulting suspension is stirred at room temperature for two hours and then 0.47 ml. of 2-chloroethyl-methyl ether are added; the reaction mixture is heated at 60° for six hours and then it is poured onto water and extracted with ether (3×30 ml); the ethereal phase is washed with water (3×20 ml), dried over anhydrous sodium sulfate and concentrated, obtaining 2.3 g of an oil. The residue is converted into the hydrogen fumarate salt in ethanolic solution. The salt is filtered off and dried yielding 0.9 g of 2-[1-((4-(1,1-dimethylethyl)phenyl)methyl)piperidine-4-yl]-1-(2-methoxyethyl)-1H-benzimidazole, hydrogen-fumarate.

Mp: 113°–116° (d).

IR (KBr), $\nu$ (cm$^{-1}$): 640, 1100, 1460, 1505, 2500–3500.

$^1$H RMN (CCl$_4$) δ: 1,2 (s, 9H, 3C$\underline{H}_3$), 1,5–2,4 (m, 4H, piperidine), 2,4–3,2 (m, 5H, piperidine), 3,1(S, 3H, OC$\underline{H}_3$), 3,4 (s, 2H, N—C$\underline{H}_2$—Ph), 3,3–3,6 (t, 2H, CH$_2$ C$\underline{H}_2$O), 3,9–4,2 (t, 2H, N—C$\underline{H}_2$—CH$_2$), 6,7–7,6 (m, 8H Ar).

EXAMPLE 2

Preparation of 2-[1-((4-(1,1-dimethylethylethyl)phenyl)methyl)piperidin-4-yl]-1-(2-ethoxyethyl)-1H-benzimidazole To a solution of 3.47 g of 2-[1-((4-(1,1-dimethylethyl)-phenyl) methyl)piperidine-4-yl]-1H-benzimidazole in 80 ml of acetonitrile, 1.38 g of potassium carbonate and 1.08 ml of 2-chloroethyl-ethyl ether are added and the mixture is refluxed for 8 hours; then is left to cool and poured onto 200 ml of water; it is extracted with ether (3×30 ml) and the ethereal layer is washed with water (3×20 ml) and dried over anhydrous sodium sulfate. The oil obtained by elimination of the ether is purified by column chromatography by using chloroform/methanol (98/2) as eluent, thus obtaining 2 g of 2-[1-((4-(1.1-dimethylethyl)phenyl(methyl) piperidine-4-yl]-1-(2-ethoxyethyl)-1H-benzimidazole. Mp: 51°–53° C.

IR (KBr), $\nu$ (cm$^{-1}$): 750, 1120, 1460, 1505, 2980

$^1$H RMN (CCl$_4$) δ: 0,7–1,0 (t, 3H, CH$_2$C$\underline{H}_3$), 1,1 (s, 9H, 3C$\underline{H}_3$), 1,4–2,1 (m, 4H, piperidine), 2,2–3,0 (m, 5H, piperidine), 2,9–3,3 (q, 2H, C$\underline{H}_2$—CH$_3$), 3,2 (s, 2H, C$\underline{H}_2$—Ph), 3,2–3,5 (t, 2H, C$\underline{H}_2$—CH$_2$—O), 3,8–4,2 (t, 2H, N—C$\underline{H}_2$CH$_2$), 6,7–7,5 (m, 8H Ar).

The product is transformed into the corresponding hydrogen fumarate (Mp: 161°–163° d) by treatment in ethanol with 0.55 g of fumaric acid.

EXAMPLE 3

Preparation of 2-[1-((4-(1,1-dimethylethyl)phenyl)methyl)piperidin-4-yl]-1-[(2-(1-methylethoxy)ethyl)]-1H-benzimidazole To a solution of 2.94 g of 2-[1-((4-(1.1-dimethylethyl)-phenyl) methyl)piperidine-4-yl]-1H-benzimidazole in 50 ml of dimethylformamide, 2.17 g of 2-[1-(methylethoxy)ethyl] tosylate and 0.45 g of sodium hydrogencarbonate are added at room temperature; the resulting suspension is stirred at room temperature for four hours and then concentrated. The residue is taken up in water and extracted with ether. The ethereal extracts were washed with water (2×20 ml) and dried over anhydrous sodium sulfate; after concentration they give an oil which is transformed into the hydrogen fumarate salt in ethanolic solution. The salt is filtered off and dried yielding 1.5 g of 2-[1-((4-(1,1-dimethylethyl)-phenyl)methyl)piperidine-4-yl]-1-(methylethoxyethyl)-1H-benzimidazole hydrogen fumarate.

Mp: 210°–212° C.

IR (KBr) (free base), $\nu$ cm$^{-1}$: 755, 1100, 1120, 1460, 1505, 2980.

$^1$H RMN (CCl$_4$) (free base) δ: 0,5–0,7 [(d, 6H CH(CH$_3$)$_2$], 0,9 (s, 9H, 3CH$_3$), 1,3–2,0 (m, 4H, piperidine), 2,2–2,9 (m, 5H, piperidine), 2,9–3,2 (m, 1H, CH), 3,1 (s, 2H, CH$_2$—Ph), 3,1–3,4 (t, 2H, CH$_2$CH$_2$O), 3,7–4,0 (t, 2H, N CH$_2$CH$_2$), 6,7–7,5 (m, 8H Ar).

EXAMPLE 4

Preparation of
2-[1-(2-(4-(1,1-dimethylethyl)-phenyl)ethyl)piperidin-4-yl]-1-[2-(1-methylethoxy)ethyl]-1H-benzimidazole To a suspension of 3.61 g of 2-[1-(2-(4-(1,1-dimethylethyl) phenyl)ethyl)piperidin-4-yl]-1H-benzimidazole in 40 ml of DMF, 0.48 g of a sodium hydride suspension in oil are added; it is stirred at room temperature for 1 hour and then a solution of 2.58 g of 2-[1-(methylethoxy)ethyl] tosylate in 20 ml of DMF are slowly added. The mixture is heated at 60° C. for 20 hours, poured onto water and extracted with ether; the ethereal layer is dried over anhydrous sodium sulfate and the solvent evaporated; the residue is purified by column chromatography yielding 2.5 g of 2- [1- (2- (4-(1,1-dimethylethyl)phenyl)ethyl)piperidine-4-yl]-1-[2-(1-methylethoxy)ethyl]-1H-benzimidazole.

Mp: 115°–117° C.

RMN (DCCl$_3$) δ: 1,0–1,1 [d, 6H, CH—(CH$_3$)$_2$], 1,3 (s, 9H, 3CH$_3$), 1,75–2,3 (m, 6H, piperidine), 2,6–2,75 (m, 2H, CH$_2$), 2,75–2,9 (m, 2H, CH$_2$), 2,95–3,1 (m, 1H, CH), 3,1–3,25 (m, 2H, piperidine), 3,65–3,75 (t, 2H, CH$_2$O), 4,25–4,35 (t, 2H, CH$_2$ N), 7,1–7,2 (m, 7H, Ar), 7,7–7,8 (m, 1H, Ar).

EXAMPLE 5

Preparation of
2-[1-(2-(4-(1,1-dimethylethyl)-phenyl)ethyl)piperidin-4-yl]-1-(2-ethoxyethyl)-1H-benzimidazole 1.5 g of a sodium hydride suspension in oil are added to another suspension of 10.83 g of 2-[1-(2-(4-(1,1-dimethylethyl)phenyl)ethyl)piperidin-4-yl]-1H-benzimidazolein 150 ml of dimethylformamide and the mixture is stirred for 1 hour at room temperature, heated at 60° C. for 16 hours, poured onto water and extracted with ether. The extracts are washed with water, dried over anhydrous sodium sulfate and concentrated. The obtained oil is purified by column chromatography yielding 6 g of 1-(2-ethoxyethyl)-2-[1-(2-(4-(1,1-dimethylethyl)phenyl)ethyl)piperidine-4-yl]-1H-benzimidazole.

Mp: 138°–140° C.

IR (KBr), $\nu$, cm$^{-1}$: 740, 1120, 1235, 1450 y 1500 cm$^{-1}$.

RMN (DCCl$_3$) δ: 1,07–1,15 (t, 3H, CH$_2$CH$_3$), 1,28 (s, 9H, 3CH$_3$), 1,95–2,3 (m, 6H, piperidine), 2,6–2,75 (m, 2H, CH$_2$), 2,75–2,9 (m, 2H, CH$_2$), 2,95–3,05 (m, 1H, CH), 3,15–3,25 (m, 2H, piperidine), 3,30–3,45 (q, 2H, CH$_2$ CH$_3$), 3,65–3,75 (t, 2H, CH$_2$O), 4,25–4,35 (t, 2H, CH$_2$N), 7,15–7,35 (m, 7H, Ar), 7,7–7,8 (m, 1H, Ar).

Antihistaminic and antiallergic properties of the compounds were evaluated in vitro and in vivo.

H$_1$-antihistaminic activity in vitro: Histamine-induced contractions of isolated guinea-pig ileum.

Distal ileum was obtained from male albino guinea pig (300–500 g). All animals were fasted overnight and killed by cervical dislocation and then exsanguinated. Segments approximately 20 cm long, were excised 5 cm above the ileocecal junction and fragments 25 mm long were suspended in a 20 ml organ bath in Tyrode solution (pH: 7.4), maintained at 37° C. and aerated with carbogen (95% O$_2$ and 5% CO$_2$). The tissue was washed by upward displacement of the bathing fluid. With an effective 1.2 g loading tension, the ileum was kept for 45 min (stabilization period). An accumulative dose-response curve for histamine was isotonically recorded with increasing concentrations and the tissue, after washing with Tyrode solution, was allowed to equilibrate. Twenty minutes later a second concentration-response curve was obtained previous addition of different concentrations of antagonist drugs. The results were calculated from the concentration-response curves for histamine at each drug concentration. All the concentrations were tested 2 to 4 times. Based on the type of antagonism observed, the pA$_2$ or pD'$_2$ were calculated (Magnus, Pflügers, Arch. Ges. Physiol. 102, 123 (1904); Arunlakshana, O. and Schild, M. O., Brit. J. Pharma. 14, 48 (1959); Van Rossum J. M., Arch. Int. Pharmacodyn. 143, 3–4, 299 (1963)). In table I the obtained results are shown.

TABLE I

In vitro antihistaminic activity of compounds of general formula I.

| Substituents | | pD'$_2$ | (n) |
|---|---|---|---|
| n | R | | |
| 1 | CH$_3$ | 6.75 | (2) |
| 1 | CH$_2$CH$_3$ | 7.08 | (4) |
| 1 | CH(CH$_3$)$_2$ | 7.30 | (4) |
| 2 | CH(CH$_3$)$_2$ | 7.00 | (4) |
| 2 | CH$_2$CH$_3$ | 7.52 | (4) |
| Astemizole | | 7.00 | (4) |
| Terfenadine | | 6.33 | (5) |

H$_1$-antihistaminic activity in vivo: Vascular permeability increase induced by histamine in rats.

Female Wistar rats (120–150 g) were used. They were fasted for 18 hours prior to the assay. Each product was administered orally at doses of 1 mg/kg (5 mg/kg when R$^1$ is a methyl group), and 1 hour later 50 µl of 0.01% (w/v) histamine solution were injected intradermally on both sides of the middle dorsal line of the rat; immediately after the histamine injection, 4 ml/kg of 0.625% Evan's blue solution in PSS were injected iv. 30 min after the dye injection, animals were sacrificed and the skin was removed. The extravasated dye sites were extracted with formamide and the dye spectrophotometrically evaluated. (Lefevbre P., Salmon J., Lecomte J. and Cauwenberge Van H., C.R. Soc. Biol. 156, 183 (1962); Udaka K., Takeuchi Y. and Movat H.Z., Proc. Soc. Exp. Biol. Med. 133, 1384 (1970). Inhibiton (%) of the histamine-induced vascular permeability increase was calculated vs a control group. The obtained results are shown in Table II.

Antiallergic activity in vivo: Vascular permeability increase induced by 48 hours homologous passive cutaneous anaphylaxis (PCA) in rats.

Female Wistar rats (120–150 g) were used. They were sensitized passively by intradermic injections of homologous ovoalbumin antiserum on both sides of the middle shaved-back line of the rat. Forty-eight hours later each test compound was administered orally at doses of 1 mg/kg (5 mg/kg when $R^1$ is a methyl group) and 1 h later PCA reaction was induced by iv injection of Evans blue solution and ovoalbumin in PSS solution. The animals were sacrificed 30 minutes after the dye injection and the skin was removed. The extravasated dye sites were extracted with formamide and the dye spectrophotometrically evaluated. (Mota, I. Life Sciences 12, 917 (1963); Mota, I. Immunology 7, 681 (1964). The inhibition (%) of the PCA-induced vascular permeability increase was calculated vs a control group. The obtained results are shown in Table II.

TABLE II

Inhibition of the increase of vascular permeability of compounds of general formula I.

| Substituents | | Increase by Histamine | Increase by P.C.A. |
|---|---|---|---|
| n | R | % | % |
| 1 | $CH_3$ | 70 | 70 |
| 1 | $CH_2CH_3$ | 70 | 47 |
| 1 | $CH(CH_3)_2$ | 50 | 40 |
| 2 | $CH(CH_3)_2$ | 25 | 30 |
| 2 | $CH_2CH_3$ | 60 | 40 |
| | Astemizole | 50 | 38 |
| | Terfenadine | 20 | 37 |

A preliminary study similar to Irwins's test in mice was carried out at doses of 100 and 300 mg/kg at 1, 2, 3, 4 and 24 hours after the treatment. As reference ketotifene was used. The results are summarized in Tables III and IV.

TABLE III

Effect on CNS of compounds of general formula I at doses of 100 mg/kg.

| 100 mg/kg Substituents | | | Affected animals/Total animals[a] | | | | | |
|---|---|---|---|---|---|---|---|---|
| n | R | Death | Spontaneous Activity decrease | Palpebral Ptosis | Hypothermia | Convulsions | Loss of right-time reflex | Loss of pinneal reflex |
| 1 | $CH_3$ | — | 3/4 | — | 2/4 | — | — | — |
| 1 | $CH_2CH_3$ | — | — | — | — | — | — | — |
| 1 | $CH(CH_3)_2$ | — | — | — | — | — | — | — |
| 2 | $CH_2CH_3$ | — | — | — | — | — | — | — |
| 2 | $CH_2CH_3$ | — | — | — | — | — | — | — |
| | Ketotifene | — | — | — | — | — | — | — |

[a]If no effects were detected, no figures are shown.

TABLE IV

Effect on CNS of compounds of general formula I at doses of 300 mg/kg.

| 300 mg/kg Substituents | | | Affected animals/Total animals[a] | | | | | |
|---|---|---|---|---|---|---|---|---|
| n | R | Death | Spontaneous Activity decrease | Palpebral Ptosis | Hypothermia | Convulsions | Loss of right-time reflex | Loss of pinneal reflex |
| 1 | $CH_3$ | 4/4 | 4/4 | 4/4 | 4/4 | 4/4 | 4/4 | 4/4 |
| 1 | $CH_2CH_3$ | — | 4/4 | — | — | 4/4 | — | — |
| 1 | $CH(CH_3)_2$ | — | — | — | — | — | — | — |
| 2 | $CH_2CH_3$ | — | — | — | — | — | — | — |
| 2 | $CH_2CH_3$ | — | 2/4 | — | — | — | — | — |
| | Ketotifene | — | 2/4 | 1/4 | 1/4 | — | 1/4 | — |

[a]If no effects were detected, no figures are shown.

In view of their antihistaminic properties, compounds of formula I and their acid addition salts are very useful in the treatment of allergic diseases such as allergic rhinitis, allergic conjunctivitis, chronic urticaria, allergic asthma and the like.

The compounds described in this invention may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carrier. For parenteral compositions, the carrier will usually comprise sterile water, at least in large part, though other ingredients, for example to aid solubility, may be added. In preparing the compositions in oral dosage form, any of the usual pharmaceutical media may be employed such as water, glycols, oils, alcohols and the like in the case of oral liquid preparations such as suspensions, syrups, elixirs and solutions; or solid carriers such as sugars, kaolin, lubricants, binders, disintegrating agents and the like in the case of powders, pills, capsules and tablets.

What is claimed is:

1. A compound of the formula

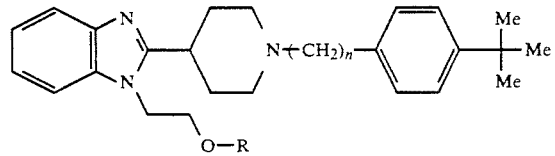

or a pharmaceutically acceptable salt thereof, wherein n is 1 or 2 and R is lower alkyl, lower alkenyl or lower cycloalkyl.

2. A compound according to claim 1, which is 2-[1-((4-(1,1-dimethylethyl)phenyl) methyl)piperidin-4-yl]-1-(2-methoxyethyl)-1H-benzimidazole or a pharmaceutically acceptable salt thereof.

3. A compound according to claim 1, which is 2-[1-((4-(1,1-dimethylethyl)phenyl) methyl)piperidin-4-yl]-1-(2-ethoxyethyl)-1H-benzimidazole or a pharmaceutically acceptable salt thereof.

4. A compound according to claim 1, which is 2-[1-((4-(1,1-dimethylethyl)phenyl methyl)piperidin-4-yl]-1-(2-methylethoxy)ethyl]-1H-benzimidazole or a pharmaceutically acceptable salt thereof.

5. A compound according to claim 1, which is 2-[1-(4-(1,1-dimethylethyl)phenyl) ethyl)piperidin-4-yl]-1-[2-(1-methylethoxy)ethyl]-1H-benzimidazole or a pharmaceutically acceptable salt thereof.

6. A compound according to claim 1, which is 2-[1-((4-(1,1-dimethylethyl)phenyl ethyl)piperidin-4-yl]-1-2-ethoxyethyl)-1H-benzimidazole or a pharmaceutically acceptable salt thereof.

7. An antihistaminic and antiallergic pharmaceutical composition comprising an inert carrier material and an effective antihistaminic or antialergic amount of a compound of the formula

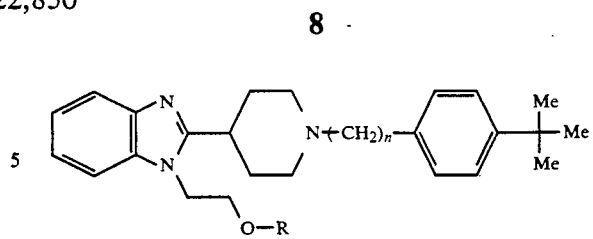

or a pharmaceutically acceptable salt thereof, wherein n is 1 or 2 and R is lower alkyl, lower alkenyl or lower cycloalkyl.

8. The composition of claim 7, wherein said compound is 2-[1-((4-(1,1-dimethylethyl)phenyl) methyl)-piperidin-4-yl]-1-(2-methoxyethyl)-1H-benzimidazole or a pharmaceutically acceptable salt thereof.

9. The composition of claim 7, wherein said compound is 2-[1-((4-(1,1-dimethylethyl)phenyl) methyl)-piperidin-4-yl]-1-(2-ethoxyethyl)-1H-benzimidazole or a pharmaceutically acceptable salt thereof.

10. The composition of claim 7, wherein said compound is 2-[1-((4-(1,1-dimethylethyl)phenyl) methyl)-piperidin-4-yl]-1-[2-(1-(methylethoxy)ethyl]-1H-benzimidazole or a pharmaceutically acceptable salt thereof.

11. The composition of claim 7, wherein said compound is 2-[1-(2-(4-(1,1-dimethylethyl)phenyl) ethyl)-piperidin-4-yl]-1-(2-[1-(2-(4-(1,1-dimethylethyl)phenyl)ethyl)piperidin-4-yl]-1-[2-(1-methylethoxy)ethyl]-1H-benzimidazole or a pharmaceutically acceptable salt thereof.

12. The composition of claim 7, wherein said compound is 2-[1-(2-(4-(1,1-dimethylethyl)phenyl) ethyl)-piperidin-4-yl]-1-2-ethoxyethyl)-1H-benzimidazole or a pharmaceutically acceptable salt thereof.

* * * * *

UNITED STATES PATENT AND TRADEMARK OFFICE
CERTIFICATE OF CORRECTION

PATENT NO. : 5,322,850
DATED : June 21, 1994
INVENTOR(S) : Aurelio ORJALES-VENERO; Victor RUBIO-ROYO It is certified that error appears in the above-indentified patent and that said Letters Patent is hereby corrected as shown below:

ON THE TITLE PAGE:

Item 73, change "Leiva-Lamiaco" to read --Leioa-Lamiaco--.

Signed and Sealed this

Seventeenth Day of October, 1995

Attest:

BRUCE LEHMAN

*Attesting Officer*   Commissioner of Patents and Trademarks